United States Patent [19]
Chou

[11] Patent Number: 6,121,511
[45] Date of Patent: Sep. 19, 2000

[54] PRODUCTION OF TRANSGENIC IMPATIENS

[75] Inventor: Tau-San Chou, Batavia, Ill.

[73] Assignee: Ball Horticultural Company, West Chicago, Ill.

[21] Appl. No.: 09/151,782

[22] Filed: Sep. 11, 1998

Related U.S. Application Data

[60] Provisional application No. 60/058,902, Sep. 12, 1997.

[51] Int. Cl.[7] .............................. C12N 5/04; C12N 15/82; C12N 15/84; C12N 15/90; A01H 5/10

[52] U.S. Cl. ...................... 800/294; 435/69.1; 435/418; 435/419; 435/430; 435/431; 800/278; 800/280; 800/281; 800/282; 800/283; 800/285; 800/286; 800/288; 800/290; 800/301; 800/302; 800/323

[58] Field of Search ............................. 435/69.1, 320.1, 435/410, 418, 419, 430, 431; 536/23.6; 800/278, 279, 280, 281, 282, 283, 285, 286, 288, 290, 294, 295, 298, 301, 302, 323

[56] References Cited

FOREIGN PATENT DOCUMENTS

| | | | |
|---|---|---|---|
| 0 354 687 | 2/1990 | European Pat. Off. .......... | A01H 5/00 |
| 0 524 910 | 1/1993 | European Pat. Off. ......... | C12N 15/55 |
| 0 566 525 | 10/1993 | European Pat. Off. ......... | C12N 15/40 |
| 95/24486 | 9/1995 | WIPO ............................. | C12N 15/29 |
| 96/29420 | 9/1996 | WIPO ............................. | C12N 15/82 |

OTHER PUBLICATIONS

Potrykus, I., Annu. Rev. Plant Physiol. Plant Mol. Biol., vol. 42, pp. 205–225, 1991.

Takeshi et al., *Shokubutsu Soshiki Baiyo* 12:73 (1995); Chem. Abs. 122(25) 310945u.

Miki et al., "Procedures for Introducing Foreign DNA into Plants," in Methods In Plant Molecular Biology and Biotechnology, Glick et al. (eds.), pp. 67–88 (CRC Press 1993).

Christou, "Application to Plants," in Particle Bombardment Technology for Gene Transfer, Yang et al. (eds.), pp. 71–99, (Oxford University Press 1994).

*Primary Examiner*—Lynette R. F. Smith
*Assistant Examiner*—Ashwin D. Mehta
*Attorney, Agent, or Firm*—Foley & Lardner

[57] ABSTRACT

Impatiens is a major ornamental bedding and potted plant, and is an important component of the U.S. floral industry. Susceptibility to insect pests and diseases caused by pathogens remains a problem for Impatiens production, even under greenhouse conditions. While chemical treatment can control certain insect pests and disease pathogens, such treatment can also have an adverse effect upon Impatiens. The methods described herein provide a means to genetically engineer transgenic Impatiens that express macromolecules capable of protecting the plant against the insects and pathogens. The production of transgenic plants can also be used to enhance the commercial value of Impatiens by controlling or enhancing native Impatiens characteristics.

37 Claims, 1 Drawing Sheet

PRODUCTION OF TRANSGENIC IMPATIENS

This Appln claims the benefit of U.S. Provisional 60/058,902 filed Sep. 12, 1997.

BACKGROUND OF THE INVENTION

1. Field of the Invention

The present invention relates to methods for producing fertile transgenic Impatiens plants, to fertile transgenic Impatiens plants, and to transgenic seeds and progeny thereof. In particular, this invention is directed to transgenic Impatiens that express at least one macromolecule that confers resistance to Impatiens pathogens, confer improved tolerance to environmental stresses, or otherwise enhance the commercial value of the plant.

2. Background

The Impatiens genus is a member of the family Balsaminaceae and comprises some five hundred to six hundred species, many of which are commercially cultivated as ornamental plants. Impatiens include plants originating from Africa, New Guinea, Celebes and Java. Grey-Wilson, IMPATIENS OF AFRICA (A. A. Balkema 1980); H. F. Winters, *Am. Hotic.*, 52, 923 (1973). The Impatiens from Africa, India and the South Pacific include respectively, *I. wallerana, I. balsamina, I. hawkeri*. Among these *I. wallerana*, also known as *I. sultani* or *I. holstii*, is probably the most commonly grown. *I. wallerana* comprises the largest market share of all bedding plants sold in the United States and therefore is an important horticultural crop.

The New Guinea Impatiens (NGI) encompasses a group of interbreeding species that include *I. schlecteri* Warb., *I. herzogii* K. Schum, *I. linearifolia* Warb., *I. mooreana* Schltr., *I. hawkeri* Bull, and other species of the same geographic origin which are interfertile. Java and Celebes Impatiens are known as *I. platypetala* Lindl. and *I. platylpetala aurantiaca* Steen, respectively. K. Han et al., *Scientia Horticulturae*, 32, 307 (1987).

Insect pests and diseases caused by pathogens can kill Impatiens even under greenhouse conditions. Illustrative insect pests include whiteflies, mealybugs, thrips, aphids, and spider mites. Impatiens are also susceptible to diseases caused by fungi. Fungal infestation include infections by Rhizoctonia and Pythium, which can cause stunting or death of Impatiens. Impatiens is also susceptible to Botrytis blight, and infection by Alternaria and Fusarium.

Furthermore, Impatiens is also subject to bacterial infection such as Pseudomonas infection. As for viral pathogens, Impatiens is primarily susceptible to infection by the tospovirus, Impatiens necrotic spot virus (INSV), but also is a known host for the related tospovirus, tomato spotted wilt virus (TSWV). Impatiens are also known to be hosts to tobacco mosaic virus (TMV), cucumber mosaic virus (CMV), and tobacco streak virus (TSV).

Although chemical treatment can control certain of these insect pests and disease pathogens, such treatment can also have an adverse effect upon Impatiens. An alternative to chemical treatment is to genetically engineer transgenic Impatiens that express polypeptides capable of protecting the plant against the insects and pathogens. The production of transgenic plants can further be used to enhance the commercial value of Impatiens by conferring resistance to environmental stresses, such as, drought, salinity, heat, cold, frost, and sun. The production of transgenic plants can further be used to enhance the commercial value of Impatiens by controlling characteristics such as flower color, leaf color, flower size and pattern, early flowering, day neutrality, free branching, dwarfness, fragrance, among others. Other desired qualities include bioluminescence, seedling and plant vigor, and flower doubleness.

Accordingly, there is a need for a method to introduce foreign genes into Impatiens to confer resistance to INSV, impart fragrance or drought tolerance, as well as other desired properties. However, there has been no report to date of the successful production of transgenic Impatiens.

On the contrary, although researchers report the isolation of genes conferring resistance to tospoviruses in general, and INSV, in particular, these references do not disclose transformation of Impatiens. For instance WO 96/29420 to De Haan, describes transgenic plants resistance to Tospovirus, but discloses only transgenic tobacco. Similarly, EP 0566525 to Van Grinsven et al., discloses DNA constructs to transform plants to achieve resistance to INSV, but discloses only *Nicotiana tabacum* and *Petunia hybrida* transformation.

Similarly, WO 95/24486 to Attenborough, et al., discloses antimicrobial proteins isolated from seed of Impatiens and transgenic plants produced from DNA constructs which encode such proteins. This reference, however, fails to report successful transformation of Impatiens disclosing instead only tobacco transformation.

Furthermore, other researchers have described Impatiens as a desirable plant for transformation with, for example, pigment-inducing DNA constructs, EP 0524910 to Van Holst et al., or phytochrome polypeptide-encoding constructs, EP 0354687 to Hershey et al. These references do not disclose, however, actual transformation of Impatiens.

Finally, Takeshi et al., *Shokubutsu Soshiki Baiyo* 12: 73 (1995); *Chem. Abs.* 122(25) 310945u, report transient gene expression in *I. balsamina* and *I. wallerana* mature pollen transformed with plasmid pBI221 via a N-2 laser method. This reference, however, fails to report stable integration of the DNA plasmid construct, or production of a transformed Impatiens plants.

Thus, a need exists for a method to stably introduce foreign genes into Impatiens to enhance viral resistance, drought resistance, and impart fragrance as well as other traits that enhance the commercial value of this important ornamental crop.

SUMMARY OF THE INVENTION

Accordingly, it is an object of the present invention to provide a method to produce transgenic Impatiens.

It is a further object of this invention to provide transgenic Impatiens that express at least one macromolecule that confers protection against disease causing pathogens. These and other objects are achieved in accordance with one embodiment of the present invention by the provision of a method for producing transgenic Impatiens plants, comprising the steps of:

(a) introducing an expression vector into a tissue explant medium to produce transformed explant, wherein said expression vector comprises a selectable marker gene and a second foreign gene, or (a') introducing two expression vectors into said tissue explant to produce transformed explant, wherein one of said expression vectors comprises a selectable marker gene, and wherein the second of said expression vectors comprises a second foreign gene;

(b) culturing said transformed explant on a selection medium;

(c) culturing said transformed explant on regeneration medium; and (d) recovering fertile transgenic plants from the transgenic explants capable of transmitting the foreign gene to progeny.

Also provided is a method of Impatiens transformation wherein the tissue explant is pre-cultured prior to introducing the expression vector in the explant wherein the explant is pre-cultured in MS medium comprising from approximately 0.5 mg/L to 2 mg/L TDZ followed by MS medium containing auxin and cytokinin, preferably approximately 0.05 to 0.2 mg/L NAA and approximately 1 to 6 mg/L Zeatin.

Also provided is a fertile transgenic Impatiens plant having stably integrated in the plant genome a foreign gene, wherein the transgenic plant is capable of transmitting the foreign gene to progeny.

DETAILED DESCRIPTION

1. Definitions

Figure 1:
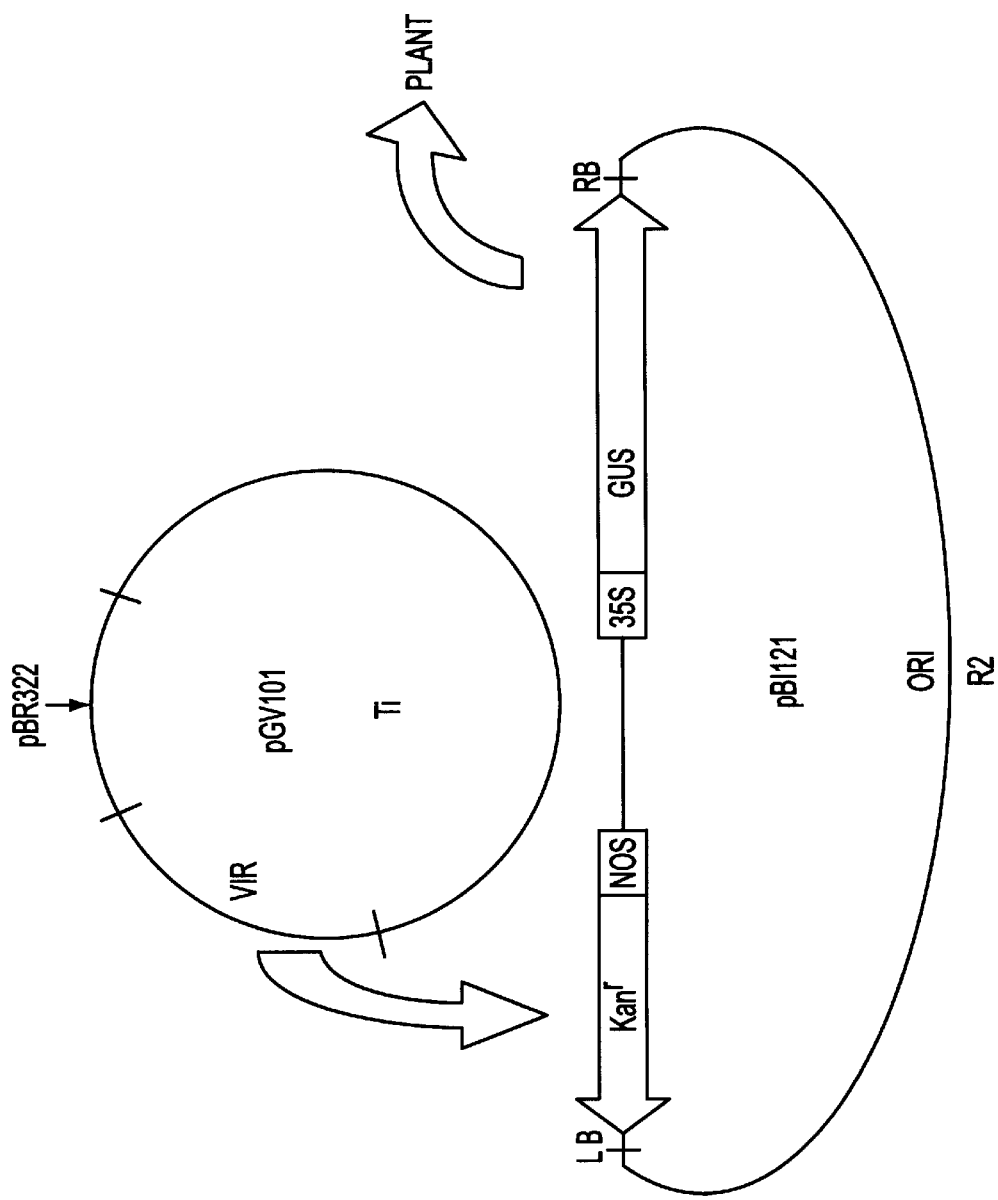
FIG. 1 is a schematic representation of plasmids pGV101 and pBI121 used in Agrobacterium transformation of Impatiens.

In the description that follows, a number of terms are used extensively. The following definitions are provided to facilitate understanding of the invention.

A structural gene is a DNA sequence that is transcribed into messenger RNA (mRNA) which is then translated into a sequence of amino acids characteristic of a specific polypeptide.

A promoter is a DNA sequence that directs the transcription of a structural gene. Typically, a promoter is located in the 5' region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter.

An isolated DNA molecule is a fragment of DNA that is not integrated in the genomic DNA of an organism. For example, a cloned *Bacillus thuringiensis* toxin gene is an illustration of an isolated DNA molecule. Another example of an isolated DNA molecule is a chemically-synthesized DNA molecule that is not integrated in the genomic DNA of an organism.

An enhancer is a DNA regulatory element that can increase the efficiency of transcription, regardless of the distance or orientation of the enhancer relative to the start site of transcription.

Complementary DNA (cDNA) is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand.

The term expression refers to the biosynthesis of a gene product. For example, in the case of a structural gene, expression involves transcription of the structural gene into mRNA and the translation of mRNA into one or more polypeptides.

A cloning vector is a DNA molecule, such as a plasmid, cosmid, or bacteriophage, that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance.

An expression vector is a DNA molecule comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements.

A foreign gene or a transgene refers in the present description to a DNA sequence that is operably linked to at least one heterologous regulatory element. For example, a cDNA molecule encoding an insect toxin is considered to be a foreign gene.

A recombinant host may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

A transgenic plant is a plant having one or more plant cells that contain an expression vector.

In eukaryotes, RNA polymerase II catalyzes the transcription of a structural gene to produce mRNA. A DNA molecule can be designed to contain an RNA polymerase II template in which the RNA transcript has a sequence that is complementary to that of a specific mRNA. The RNA transcript is termed an antisense RNA and a DNA sequence that encodes the antisense RNA is termed an antisense gene. Antisense RNA molecules are capable of binding to mRNA molecules, resulting in an inhibition of mRNA translation.

A ribozyme is an RNA molecule that contains a catalytic center. The term includes RNA enzymes, self-splicing RNAs, and self-cleaving RNAs. A DNA sequence that encodes a ribozyme is termed a ribozyme gene.

An external guide sequence is an RNA molecule that directs the endogenous ribozyme, RNase P, to a particular species of intracellular mRNA, resulting in the cleavage of the mRNA by RNase P. A DNA sequence that encodes an external guide sequence is termed an external guide sequence gene.

Impatiens as used herein includes species of the genus Impatiens as known to a skilled artisan, including selections of Africa, India, New Guinea, Java, and Celebes origin. Furthermore, the present invention can be used with both seed and vegetatively propagated Impatiens plant material.

A fertile transgenic plant is a plant containing a foreign gene stably transformed into its genome including the nuclear, mitochondrial, and/or chloroplast genomes which is capable of transmitting the foreign gene to progeny via sexual reproduction.

2. Methods for Producing Transgenic Impatiens

The procedures described herein provide a means to produce fertile transgenic Impatiens that contain an expression vector, and that express at least one foreign gene which can be transmitted to progeny.

The foreign gene can be introgressed into other Impatiens plants by traditional breeding methods, well known to the skilled artisan. For example, the fertile transgenic Impatiens plant is crossed to non-transgenic Impatiens selections in order to combine the foreign gene with other traits of agronomic interest. Alternatively, a transgenic Impatiens plant containing a first foreign gene is crossed to a second fertile transgenic Impatiens plant containing a second foreign gene to produce progeny in which the first and second foreign genes are combined in the same plant selection. Methods for the vegetative or sexual propagation of Impatiens are well known. See, for example, Ball, V. (ed), Ball RedBook, Ball Publ, Batavia IL, pg. 567–583 (1998). Likewise, methods for breeding with Impatiens are well known including production of F1 hybrids.

The selection of an appropriate expression vector will depend upon the method of introducing the expression vector into host cells. Typically, an expression vector contains: (1) prokaryotic DNA elements coding for a bacterial replication origin and an antibiotic resistance marker to provide for the growth and selection of the expression vector in the bacterial host; (2) eukaryotic DNA elements that control initiation of transcription, such as a promoter; (3) DNA elements that control the processing of transcripts, such as a transcription termination/polyadenylation sequence; and (4) a foreign gene operably linked to the DNA elements that control transcription initiation. Optionally, an expression vector can also contain a selectable marker gene, as described below.

Expression vectors can be introduced into protoplasts, or into intact tissues or isolated cells. General methods of culturing plant cells and tissues are provided, for example, by Miki et al., "Procedures for Introducing Foreign DNA into Plants," in METHODS IN PLANT MOLECULAR BIOLOGY AND BIOTECHNOLOGY, Glick et al. (eds.), pages 67–88 (CRC Press, 1993), and by Dixon et al., PLANT CELL CULTURE: A PRACTICAL APPROACH, $2^{nd}$ Edition (IRL Press 1994).

Methods of introducing expression vectors into plant tissue include direct gene transfer method such as microprojectile-mediated delivery, DNA injection, electroporation, and the like. See, for example, Gruber et al., infra; Miki et al., supra; Klein et al., Biotechnology 10:268 (1992).

For example, expression vectors can be introduced into plant tissues using microprojectile-mediated delivery with a biolistic device. A generally applicable method of plant transformation is microprojectile-mediated transformation wherein DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford et al., Part. Sci. Technol. 5:27 (1987), Sanford, Trends Biotech. 6:299 (1988), Sanford, Physiol. Plant 79:206 (1990), and Klein et al., Biotechnology 10:268 (1992).

Expression vectors are also introduced into plant tissues via direct infection or co-cultivation of plant tissue with Agrobacterium tumefaciens. Horsch et al., Science 227:1229 (1985). Descriptions of Agrobacterium vector systems and methods for Agrobacterium-mediated gene transfer are provided by Gruber et al., "Vectors for Plant Transformation," in METHODS IN PLANT MOLECULAR BIOLOGY AND BIOTECHNOLOGY, Glick et al. (eds.), pages 89–119 (CRC Press, 1993), Miki et al., supra, and Moloney et al., Plant Cell Reports 8: 238 (1989).

Additionally, expression vectors may be introduced into the plant chloroplast genome by methods well known to the skilled artisan. See, U.S. Pat. Nos. 5,451,513 and 5,693,507. Foreign genes introduced into the chloroplast genome are maternally inherited.

Transcription of the foreign gene may be controlled by a plant promoter or by a viral promoter, such as a Cauliflower Mosaic Virus (CaMV) 35S promoter and its derivative, the enhanced 35S version ("E35S"), a Figwort Mosaic Virus promoter, and the like. Gruber et al., supra. Odell et al., Nature 313:810 (1985); Kay et al., Science 236:1299 (1987). The polyubiquitin gene promoters from Arabidopsis thaliana, UBQ3 and UBQ10, Norris et al., Plant Mol. Biol. 21:895 (1993), are also useful for directing gene expression in transgenic Impatiens. Additional useful promoters from Arabidopsis include the TEFA 1 gene promoter from the Arabidopsis translation elongation factor 1 gene and two additional polyubiquitin gene promoters from Arabidopsis, UBQ11 and UBQ14. Norris et al., Plant Mol. Biol. 21:895 (1993); Callis et al., Genetics 139:921 (1995). Of these promoters, the preferred promoters are the 35S promoter, the E35S promoter, the UBQ3 promoter, and the UBQ10 promoter.

Other promoters that are useful for phloem-specific expression of transgenes in Impatiens include the rolC gene promoter from Agrobacterium rhizogenes and the Commelina Yellow Mottle Virus (CoYMV) promoter which have been shown to direct high levels of transgene expression in the phloem of transgenic plants. Medberry and Olszewski, Plant J. 3:619 (1993); Nilsson et al., Plant Mol. Biol. 31:887 (1996).

In order to select transformed cells, the expression vector contains a selectable marker gene, such as a herbicide resistance gene or an antibiotic resistance gene. For example, the neomycin phosphotransferase gene (nptII gene) confers resistance to kanamycin and G418, the aminoglycoside phosphotransferase IV gene (hygromycin phosphotransferase gene of E. coli) confers resistance to hygromycin, the phosphinothricin acetyltransferase gene confers resistance to phosphinothricine, the dihydrofolate reductase gene confers resistance to methotrexate, the 5-enolpyruvylshikimate-3-phosphate synthase gene confers resistance to glyphosate, the acetohydroxyacid synthase gene confers resistance to sulfonyl ureas and imidazolinones, chloramphenicol resistance is provided by the chloramphenicol acetyltransferase gene, and the 3"-adenylyltransferase gene confers resistance to spectinomycin and streptomycin. Fraley et al., Proc. Natl. Acad. Sci. U.S.A. 80:4803 (1983). Gritz and Davies, Gene 25:179 (1983), Wilmink and Dons, Plant Molec. Biol. Report. 11:165 (1993).

Additional selectable marker genes of bacterial origin that confer resistance to antibiotics include gentamycin acetyltransferase, streptomycin phosphotransferase, aminoglycoside-3'-adenyl transferase, the bleomycin resistance determinant. Hayford et al., Plant Physiol. 86:1216 (1988), Jones et al., Mol. Gen. Genet. 210:86 (1987), Svab et al., Plant Mol. Biol. 14:197 (1990), Hille et al., Plant Mol. Biol. 7:171 (1986). Other selectable marker genes confer resistance to herbicides such as glyphosate, glufosinate or broxynil. Comai et al., Nature 317:741 (1985), Gordon-Kamm et al., Plant Cell 2:603 (1990), and Stalker et al., Science 242:419 (1988). Still other selectable markers confer a trait that can be identified through observation or testing, for example, β-glucuronidase or uidA gene (GUS) which encodes an enzyme for which various chromogenic substrates are known. Jefferson, et al., EMBO 6:3901 (1987).

The use of such selectable marker genes is well-known to those of skill in the art. See, for example, Christou, "Application to Plants," in PARTICLE BOMBARDMENT TECHNOLOGY FOR GENE TRANSFER, Yang et al. (eds)., pages 71–99 (Oxford University Press 1994). The nptII gene is a preferred selectable markers.

Post-transcriptional events such as processing of the 3'-end of a transcript and polyA addition are important steps of gene expression. Accordingly, expression vectors typically include DNA elements that control the processing of transcripts, such as a transcription termination/polyadenylation sequence. The 3'-flanking region from the nopaline synthase gene (nos) of *Agrobacterium tumefaciens* has proven to be a very efficient and versatile cis-acting sequence for transgene expression.

The expression vector can contain cDNA sequences encoding a foreign protein, as well as the selectable marker gene each under the control of a different promoter. Alternatively, the selectable marker gene can be delivered to host cells in a separate selection expression vector by co-transformation with both vectors.

The present invention also contemplates the production of transgenic Impatiens comprising an expression vector that produces antisense RNA. The binding of antisense RNA molecules to target mRNA molecules results in hybridization arrest of translation. Paterson, et al., *Proc. Natl. Acad. Sci. USA*, 74: 4370 (1987). A suitable antisense RNA molecule, for example, would have a sequence that is complementary to that of a viral mRNA species encoding a protein necessary for proliferation of the virus.

Alternatively, an expression vector can be constructed that produces a ribozyme. Ribozymes can be designed to express endonuclease activity that is directed to a certain target sequence in a mRNA molecule. For example, Steinecke et al., *EMBO J.* 11:1525 (1992), achieved up to 100% inhibition of neomycin phosphotransferase gene expression by ribozymes in tobacco protoplasts. Similarly, Perriman et al., *Antisense Research and Development* 3:253 (1993), inhibited chloramphenicol acetyltransferase activity in tobacco protoplasts using a vector that expressed a modified hammerhead ribozyme. In the context of the present invention, appropriate target RNA molecules for ribozymes include mRNA species that encode viral proteins.

In another approach to providing protection against virus infection, expression vectors can be constructed in which a promoter directs the production of RNA transcripts capable of stimulating RNase P-mediated cleavage of target mRNA molecules. According to this approach, an external guide sequence can be constructed for directing the endogenous ribozyme, RNase P, to a particular species of intracellular mRNA, which is subsequently cleaved by the cellular ribozyme. Altman et al., U.S. Pat. No. 5,168,053. Yuan et al., *Science* 263: 1269 (1994). Preferably, the external guide sequence comprises a ten to fifteen nucleotide sequence complementary to an mRNA species that encodes a protein essential for viral reproduction, and a 3'-NCCA nucleotide sequence, wherein N is preferably a purine. The external guide sequence transcripts bind to the targeted mRNA species by the formation of base pairs between the mRNA and the complementary external guide sequences, thus promoting cleavage of mRNA by RNase P at the nucleotide located at the 5'-side of the base-paired region.

The preferable procedure for producing transgenic Impatiens includes harvesting and pre-culturing Impatiens tissue explants, preferably shoot tips, hypocotyl tips or node regions, most preferably shoot tips. However, Impatiens tissue explants may be directly transformed and transformed explants, selected and regenerated into fertile transgenic plants. Any Impatiens plant can be transformed by the claimed method. Preferred Impatiens varieties include the seed Impatiens, such as, Super Elfin Scarlet, Super Elfin Twilight, and the New Guinea Impatiens, such as, Celebration Red, Celebration Deep Pink, Celebration Candy Pink and Celebration Cherry Star. Most preferably, the variety used is seed Impatiens Super Elfin Twilight or New Guinea Impatiens Celebration Deep Pink (U.S. Plant Patent No. 8409).

Pre-culturing medium comprises medium described by Murashige and Skoog, *Physiol. Plant* 15: 473 (1962) (MS Medium) supplemented with ingredients selected from the following approximate combinations:

TABLE 1

Zeatin (4-hydroxy-3-methyl-trans-2-butenylaminopurine) 1 mg/L
2 ip (N-2-isopentyl adenine) 15 mg/L
BAP (6-benzylaminopurine) 15 mg/L
2 ip 20 mg/L, BAP 20 mg/L
2 ip 20 mg/L, Kinetin (6-furfurylaminopurine) 20 mg/L
2 ip 20 mg/L, BAP 10 mg/L, IAA (3-indole-acetic-acid) 0.01 mg/L
2 ip 20 mg/L, Kinetin 10 mg/L, IAA 0.01 mg/L
2 ip 20 mg/L, Zeatin 1 mg/L, IAA 0.01 mg/L
NAA (1-naphthylacetic acid) 0.9 mg/L, BAP 2.25 mg/L
2, 4-D (2,4-dichlorophenoxyacetic acid) 0.8 mg/L, 2 ip 0.4 mg/L
NAA 0.2 mg/L, Zeatin 6 mg/L
NAA 0.05 mg/L, Zeatin 6 mg/L
TDZ (1-phenyl-3-9],2,3-thiadiazol-5-yl) urea) 1 mg/L Preferably, explants are pre-cultured in a liquid MS medium containing TDZ (1 mg/L) for 5 days. Subsequently, the explants are preferably subcultured on a solid MS medium supplemented with NAA 0.05 mg/L and Zeatin 6 mg/L for 48 hours.

Next, an expression vector is introduced into the pre-cultured explant via gene transfer methods known to those of skill in the art such as microparticle bambardment or Agrobacterium-mediated transformation. With regard to Agrobacterium-mediated transformation, the explant is suspended in an Agrobacterium suspension and is then wounded to facilitate inoculation. A preferred Agrobacterium gene-transfer system is the binary vector system, such as pBI121 containing the Agrobacterium T-DNA region, nptII gene, and a second foreign gene, Jefferson, et al., supra, and a helper plasmid, pGV101 containing the Ti plasmid Vir region.

Next, the transformed explant is blot dry treated and transferred to fresh medium, preferably MS medium supplemented with approximately 0.05 mg/L NAA and 6 mg/L Zeatin without antibiotics for approximately two days. At which time, the explant may be transferred to selection medium, preferably comprising, MS medium supplemented with approximately 0.05 mg/L NAA and 6 mg/L Zeatin medium, further supplemented with the following antibiotic concentrations: approximately 500 mg/L carbenicillin, 100 mg/L. kanamycin, and 100 mg/L cefotaxmine.

The explant is then subcultured approximately every week on regeneration medium, preferably, MS medium containing further ingredients selected from Table 1, more preferably being MS medium supplemented with approximately 0.05 mg/L NAA and 6 mg/L Zeatin, optionally containing selection ingredients, such as the antibiotics mentioned above, until axillary shoots develop. The above methods for transforming Impatiens may be supplemented or varied according to known methods for Impatiens shoot regeneration as exemplified by Stephens, et al., *HortScience* 20:362 (1985); Han, et al., *Sci. Hortic.* 32:307 (1987); Han, K. In vitro shoot regeneration from cotyledons of immature ovules of *Impatiens platypetala* Lindl., which are herein incorporated by reference. The regenerated plants are fertile and capable of transmitting a foreign gene to progeny.

3. Production of Transgenic Impatiens Expressing a Foreign Gene That Enhances Commercial Value (a) Inhibition of Plant Pests and Diseases The present invention provides a means to control insect pests and diseases of Impatiens plants. Impatiens are subject to attack by insect pests and pathogen-induced diseases under greenhouse conditions. Insect pests include whitefly, mealybugs, aphids, or thrips.

Impatiens are also susceptible to diseases caused by fungi and bacteria. As for fungi, Impatiens are hosts to Rhizoctonia (*Rhizoctonia solani*), Pythium, Botrytis (*Botrytis cinerea*), Fusarium, and Alternaria.

Bacteria infect Impatiens primarily through wounds such as the surface of a cutting made for vegetative propagation, or natural openings, such as hydathodes, lenticels, nectaries, and stomates.

The most notable viral pathogen of Impatiens the tospovirus, Impatiens necrotic spot virus (INSV), but also is a known host for the related tospovirsu, tomato spotted wilt virus (TSWV), which causes symptoms similar to INSV. Impatiens are also known to be hosts to tobacco mosaic virus (TMV), cucumber mosaic virus (CMV), and tobacco streak virus (TSV).

As a protection against insect pests, transgenic Impatiens can be produced that express insecticidal toxin genes. For example, the gram-positive bacterium *Bacillus thuringiensis* produces polypeptides that are toxic to a variety of insect pests, but have no activity against vertebrates and beneficial insects. Thompson, "Biological Control of Plant Pests and Pathogens: Alternative Approaches," in BIOTECHNOLOGY IN PLANT DISEASE CONTROL, Chet (ed.), pages 275–290 (Wiley-Liss, Inc. 1993). Suitable Bacillus thuringiensis toxins include cryIA δ-endotoxins which are highly toxic to lepidopteran insects and cryIIIA δ-endotoxins which are highly toxic to coleopteran insects.

Geiser et al., *Gene* 48: 109 (1986), disclose the cloning and nucleotide sequence of a cryIA(b) δ-endotoxin gene. The transformation of plants with vectors comprising a cryIA(b) δ-endotoxin gene has been described by Williams et al., *Bio/Technology* 10: 540 (1992), Koziel et al., *Bio/Technology* 11: 194 (1993), and Fujimoto et al., *Bio/Technology* 11: 1151 (1993). Lereclus et al., *Bio/Technology* 10: 418 (1992), disclose the construction of a plasmid comprising structural genes encoding for cryIIIA and cryIAc. In addition, Adang et al., *Plant Molec. Biol.* 21: 1131 (1993), disclose the nucleotide sequence of a synthetic cryIIIA gene which was designed for optimal expression in plant cells. Moreover, DNA molecules encoding δ-endotoxin genes can be purchased from American Type Culture Collection (Rockville, Md.), under ATCC accession Nos. 40098, 67136, 31995 and 31998.

Insecticidal toxins which are suitable for production of transgenic Impatiens include (1) a vitamin-binding protein such as avidin; (2) an enzyme inhibitor, for example, a protease inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), and Sumitani et al., *Biosci. Biotech. Biochem.* 57:1243 (1993) (nucleotide sequence of *Streptomyces nitrosporeus* α-amylase inhibitor); (3) an insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone; (4) an insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also Tomalski et al., U.S. Pat. No. 5,266,317, who disclose genes encoding insect-specific, paralytic neurotoxins; (5) an insect-specific venom produced in nature by a snake, a wasp, etc. For example, see Pang et al., *Gene* 116:165 (1992), for disclosure of heterologous expression in plants of a gene coding for a scorpion insectotoxic peptide; (6) an enzyme responsible for an hyperaccumulation of a monoterpene, a sesquiterpene, a steroid, hydroxamic acid, a phenylpropanoid derivative or another non-protein molecule with insecticidal activity; (7) an enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See Scott et al., PCT application WO 93/02197, who disclose the nucleotide sequence of a callase gene. DNA molecules which contain chitinase-encoding sequences can be obtained, for example, from the ATCC under accession Nos. 39637 and 67152. See also Kramer et al., *Insect Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi4-2 polyubiquitin gene; (8) a molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone; or (9) an insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (1994) (enzymatic inactivation in transgenic tobacco via production of single-chain antibody fragments).

As discussed above, chitinase genes are useful for inhibiting insect pests. Chitinase also can be used for combating fungal pathogens. Methods for producing transgenic plants that express chitinase are described, for example, by Suslow et al., U.S. Pat. No. 5,554,521 (1996), and by Jaynes et al., U.S. Pat. No. 5,597,946 (1997). Additional antifungal genes include genes encoding β-1,3-glucanase, which degrades a major polysaccharide of fungal cell walls, and ribosome-inactivating protein, which inactivates fungal ribosomes. Full-length cDNAs of glucanase and ribosome-inactivating protein are disclosed in Leah et al., *J. Biol. Chem.* 266:1564 (1991). In addition, Logemann et al., *Bio/Technology* 10:305 (1992), demonstrate that the expression of a foreign ribosome-inactivating protein increases resistance to fungal disease in transgenic plants.

Those of skill in the art are aware of additional polypeptides useful to protect plants against bacterial and fungal pathogens. See, for example, Düring, *Molec. Breeding* 2:297

(1996). Such polypeptides include the bactericidal native and recombinant cecropins, insect attacin, frog magainin, cereal thionins, T4 and hen egg white lysozymes, horseshoe crab tachyplesin I, Erwinia oligogalacturonide lyase. Moreover, a variety of plant disease resistance genes are available for use. Bent, *The Plant Cell* 8:1757 (1996).

Preferred antibacterial and antifungal genes include DNA molecules that encode natural and synthetic lytic peptides and plant defensins. Lytic peptides are broad-spectrum antibiotic peptides that are active against Gram-negative and Gram-positive bacteria, fungi and protozoa. These peptides can be classified into many categories based upon their structure (e.g., linear vs. cyclic), their size (20–45 amino acids) and their source (e.g., insect, amphibian, plant). However, despite their apparent diversity, numerous defense-related peptides have the common features of being highly basic and being capable of forming amphipathic structures. These unifying features suggest that most peptides appear to act by a direct lysis of the pathogenic cell membrane. Their basic structure facilitates their interaction with the cell membrane, and their amphipathic nature allow them to be incorporated into the membrane ultimately disrupting its structure.

Frog skin secretions of the African clawed frog, *Xenopus laevis*, have been discovered to be a particularly rich source of antibiotic peptides. Known peptides include magainins, $PGL^a$, xenopsin, and caerulein. Gibson et al., *J. Biol. Chem.* 261:5341 (1986); Jacob and Zasloff, *Ciba Found. Symp.* 186:197 (1994); James et al., *Anal. Biochem.* 217:84 (1994); Maloy and Kari, *Biopolymers* 37:105 (1995); Wechselberger and Kreil, *J. Molec. Endocrinol.* 14:357 (1995). Magainins 1 and 2 have 23 amino acid residues in length, contain no cysteine, and form an amphipathic α-helix. $PGL^a$ is a small peptide processed from a larger precursor and is both cationic and amphipathic in nature. It has the somewhat unusual feature of containing a COOH-terminal amide group rather than the expected carboxyl group. Moreover, it has been reported that magainin 2 (but not magainin 1) and $PGL^a$ can interact synergistically with one another to exert enhanced levels of anti-microbial activity. Westerhoff et al., *Eur. J. Biochem.* 228:257 (1995).

Insects have also been demonstrated to possess a variety of defense-related peptides. Cecropins from moths and flies are slightly larger than the frog-derived peptides (31–39 residues), are basic due to the presence of multiple arginine and lysine residues, and therefore interact strongly with the negatively charged lipid bilayers. Boman, *Cell* 65:205 (1991). Studies of these peptides have shown that they form an N-terminal α-helical region connected by a hinge region to a C-terminal α-helical domain.

In addition to the naturally-occurring peptides, a wide array of synthetic analogs representing deletion, substitution and variable chain length derivatives have been generated for structure/activity relationship studies. A number of these synthetic variants exhibit increased antimicrobial activity against bacteria and fungi. Moreover, in some cases, not only has the anti-microbial potency of the synthetic lytic peptides increased dramatically, but their spectrum of anti-microbial activity has also broadened.

The isolation and characterization of plant defensins from a number of plant species has revealed that these small peptides possess potent anti-microbial activity. Broekaert et al., *Plant Physiol.* 108:1353 (1995); Epple et al., *FEBS Lett.* 400:168 (1997). One of these defensins, Rs-AFP2 from radish seeds, has been extensively characterized. Terras et al., *Plant Cell* 7:573 (1995). A cDNA molecule that encodes this peptide has been cloned and overexpressed in tobacco. Transgenic tobacco which accumulate high levels of this peptide show enhanced resistance to infection by the fungal pathogen, *Alternaria longipes*.

Preferred insect resistance genes include DNA molecules that encode tryptophan decarboxylase (TDC) and lectins. TDC catalyzes the decarboxylation and conversion of L-tryptophan into tryptamine. Tryptamine and secologanin, another secondary compound, are then condensed to form strictosidine, the precursor for all terpenoid indole alkaloids in *Catharanthus roseus* (periwinkle). The cloning and characterization of a TDC cDNA molecule from Catharanthus seedlings has been described by De Luca et al., *Proc. Nat'l Acad. Sci. USA* 86:2582 (1989).

Thomas et al., *Plant Physiol.* 109: 717 (1995) demonstrated that tobacco plants which accumulated tryptamine adversely affected the development and reproduction of *Bemisia tabaci* (sweet potato whitefly). Whitefly emergence tests revealed that pupae emergence (to adulthood) on tryptamine-accumulating plants was typically reduced three to seven-fold relative to control plants. They speculated that tryptamine may exert its anti-whitefly effect(s) during either larval and pupal development and/or adult selection of a leaf for feeding and oviposition. Studies with the TDC gene are presented below.

An alternative anti-whitefly strategy focuses on the use of lectins to disrupt the normal life cycle of insect pests. A considerably large number of artificial feeding studies have shown that a wide range of insects are susceptible to these compounds. One particular lectin, isolated from *Galanthus nivalis* (snowdrop plant), has been demonstrated to exhibit anti-insect activity against phloem-feeders like aphids and leafhoppers. The production of transgenic Impatiens that express GNA lectin is described below.

In one approach for providing protection against viral infections, transgenic imatiens express a viral protein. The accumulation of viral coat or replicase proteins in transformed plant cells provides resistance to viral infection and/or disease development by the virus from which the coat protein gene was derived, as well as by related viruses. See Beachy et al., *Ann. Rev. Phytopathol.* 28: 451 (1990); Beachy, "Virus Resistance Through Expression of Coat Protein Genes," in BIOTECHNOLOGY IN PLANT DISEASE CONTROL, 3rd Edition, Chet (Ed.), pages 89–104 (Wiley-Liss, Inc. 1993). For example, coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. Id.

Alternatively, protection against viral disease can be achieved using a vector that expresses mammalian 2'-5' oligoadenylate synthetase. Truve et al., *Bio/Technology* 11: 1048 (1993), disclose the cloning and nucleotide sequence of a rat cDNA encoding 2'-5' oligoadenylate synthetase, a component of the mammalian interferon-induced antivirus response. Truve et al., also disclose that transgenic plants expressing 2'-5' oligoadenylate synthetase are protected against viral infection under field conditions.

In a third approach to providing protection against viral infection, a transgenic imatiens expresses a viral genome antisense RNA. For example, antisense RNA has been used to confer resistance to cucumber mosaic virus, as disclosed by Rezaian et al., *Plant Molec. Biol.* 11: 463 (1988). Moreover, Day et al., *Proc. Nat'l. Acad. Sci.* 88: 6721 (1991), have demonstrated the use of antisense RNA to confer resistance to tomato golden mosaic virus.

In a fourth approach to providing protection against viral infection, a transgenic imatiens expresses pokeweed antiviral protein (PAP), a ribosome-inhibiting protein found in the cell walls of *Phytolacca americana*. Lodge et al., *Proc. Nat'l Acad. Sci USA* 90: 7089 (1993), for example, show that PAP-expressing transgenic plants are resistant to a broad spectrum of plant viruses. Lodge et al. also disclose a method for isolating PAP cDNA.

Alternatively, protection against INSV and TSWV has been described in EP 0566525 to Van Grinsven et al. and WO 96/29420 to De Haan, respectively. EP 0566525 describes the cloning of DNA constructs encoding TSWV putative viral movement protein, and reports conferring TSWV resistance to tobacco transformed with this construct. WO 96/29420 describes the cloning of DNA constructs encoding INSV RNAs, S, M, and L, and reports methods for using such constructs to confer INSV resistance to *Nicotania tabacum* and *Petunia hybrida*.

(b) Expression of Foreign Genes That Confer Tolerance to Environmental Stresses

Impatiens growers seek to produce plants with increased tolerance to environmental stresses such as drought, salinity and cold. A variety of genes have been shown to confer increased tolerance of drought, salinity and cold. Such genes include *E. coli* MnSOD gene (U.S. Pat. No. 5,538,878 to Thomas et al.), asparagine synthetase gene and asparagine synthetase promoter (U.S. Pat. No. 5,595,896 to Coruzzi et al.), Delta$^1$-Pyrroline-5-Carboxylate Synthetase gene (U.S. Pat. No. 5,639,950 to Verma et al.; Kishor et al., *Plant Physiol* 108:1387 (1995)), bacterial fructan genes (Piloin-Smits et al., *Plant Physiol.* 107:125 (1995)), CAP85 and CAP160 genes (WO 94/17186 to Guy et al., and turgor-responsive gene trg-31 (Guerrero et al., *Plant Mol. Biol.* 21:929 (1993)). With the present invention, these genes can be employed to enhance tolerance to environmental stresses in Impatiens.

(c) Expression of Foreign Genes That Affect Impatiens Plant Habit, Fragrance and Color Impatiens growers seek to also produce plants that have variegated foliage, enhanced germination, increased plant vigor, increased flower size and petal number, dwarfness or increased branching.

Impatiens growers also seek to produce plants which are more compact (with short internodes and free branching), earlier to flower, and with bright and distinctly colored bracts. Although Impatiens have not been produced having fragrance, this would be a desirable new consumer trait.

A variety of genes have been shown to create a more compact habit and earlier flowering in transgenic plants. These include the rol genes (A, B, and C) from *Agrobacterium rhizogenes* (U.S. Pat. No. 5,648,598), phytochrome genes such as phyA (McCormac et al., *Planta* 185: 162–170 (1991)), developmental genes such as lfy (Wegel and Nilsson, *Nature* 377: 495–496 (1995)), and the MADS-box containing family of genes such as apetala (Mandel and Yanofski, *Nature* 377: 522–524 (1995)), and OsMADS1 (Chung et. al., *Plant Mol. Biol.* 26: 657–665, (1994)). With the present invention, these genes can be employed to improve the habit and reduce the flowering time of imatiens, most preferably the genes OsMADS1 or phyA.

A variety of genes have been shown to create modified color expression in transgenic plants. These include the crtO gene which can lead to the synthesis of the bright red pigment called astaxanthin, the lycopene cyclase gene which can lead to the synthesis of the orange pigment β-carotene, the β-carotene hydroxylase gene which can lead to the synthesis of the golden pigment zeaxanthin, as well as the genes in the flavonoid biosynthesis pathway which leads to the various anthocyananin pigments which can be red, blue, pale yellow, as well as a wide range of intermediates and pastels. With the present invention these genes can be employed to expand the color range in Impatiens. The preferred genes are crtO and lycopene cyclase.

Several genes have been cloned which affect plant fragrance. These genes include, but are not limited to, the linalool synthase gene which causes the synthesis of aromatic linalool and the limonene synthase gene which causes synthesis of the fragrant limonene (Alonsa et al., *J. Biol. Chem.* 267: 7582–7587 (1992).

Furthermore, tissue specific promoters have been reported for targeting genes for epidermal specific expression. For instance, U.S. Pat. No. 5,646,333 to Dobres et al. reports an epidermal specific Blec plant promoter useful for transforming plants with foreign fragrance enhancing genes. Therefore, with the present invention, genes which affect plant fragrance can be employed with epidermal specific promoters to create novel fragrances in Impatiens.

Ethylene is a key regulator in plant growth and development. Ethylene affects seed germination, stem and root elongation, flower initiation, and senescence of leaves and flowers. Many important floricultural products are very sensitive to ethylene, and under current practice, plants are treated with silver thiosulfate to eliminate ethylene sensitivity. This practice, however, is being phased out because the use of silver thiosulfate has negative environmental consequences.

Another means to confer ethylene insensitivity is to produce plants expressing a gene that affects the synthesis or perception of ethylene. Researchers have identified proteins associated with mutations in ethylene receptors or factors involved in ethylene signal transduction. For example, the Arabidopsis etr-1 and the tomato NR genes encode mutated receptors that confer dominant ethylene insensitivity. See, for example, Chang et al., *Science* 262: 539 (1993) and Wilkinson et al., *Science* 270: 1807 (1995). Moreover, the report of Wilkinson et al., *Nature Biotechnology* 15: 444 (1997), shows that the etr1-1 causes significant delays in flower senescence and flower abscission when expressed in transgenic petunia plants.

Accordingly, the present invention contemplates the production of transgenic imatiens expressing a gene that confers ethylene insensitivity. Suitable genes are exemplified by genes that encode mutated ethylene receptors, such as the Arabidopsis etr1-1 and the tomato NR genes. Such plants are less likely to suffer injury during shipment or in retail outlet environments and will therefore be of higher quality and more attractive.

Another gene that can be used to enhance imatiens plants is the Vitreoscilla hemoglobin gene ("vhb gene"), which is expressed by bacteria under oxygen-limited conditions. Khosla and Bailey, *Nature* 331:633 (1988). Holmberg et al., *Nature Biotechnology* 15:244 (1997), have shown that transgenic tobacco plants that express the vhb gene exhibit enhanced growth and a reduction in germination time, presumably due to an increased availability of oxygen and/or energy in the plant cells. Accordingly, the present invention also contemplates the production of transgenic imatiens plants that express the vhb gene.

Cytokinins are believed to play a role in leaf senescence because a decline in leaf cytokine levels occurs in senescing leaves, while the external application of cytokinin can delay senescence. Additional evidence for the role of cytokinins was provided by the demonstration that the expression of a gene encoding isopentenyl transferase, the enzyme that catalyzes the rate-limiting step in cytokinin biosynthesis, in transgenic tobacco inhibited leaf senescence. Gan and Amasino, *Science* 270:1966 (1995). In this study, the expression of the isopentenyl transferase (IPT) gene was specifically targeted to senescing leaves and was negatively auto-regulated to prevent overproduction of cytokinins. This was achieved by constructing an expression cassette comprising the IPT gene operatively linked to a promoter of an Arabidopsis senescence-associated gene, designated SAG12.

Thus, transgenic imatiens can be produced that are characterized by a decreased rate of leaf senescence. Such imatiens plants express the IPT gene, which is under the control of a promoter of a senescence-associated gene, such as the promoter of the SAG12 gene.

Studies have shown that floral organ development is controlled by a group of regulatory factors that contain a conserved MADS box domain, which is believed to be a DNA-binding domain. Schwarz-Sommer et al., *EMBO J.* 11:251 (1992). Genes that contain the MADS domain include the *Antirrhinum majus* PLENA gene, the *A. majus* SQUAMOSA gene, the *A. majus* DEFICIENS A gene, the *A. majus* GLOBOSA gene, the *Arabidopsis thaliana* APTELA1 and APETALA3 genes, the Arabidopsis AGAMOUS gene, and rice OsMADS24 and OsMADS45 genes. Bradley et al., *Cell* 72:85 (1993); Huijser et al., *EMBO J.* 11:1239 (1992); Brochman et al., *Cell* 68:683 (1992); Mandel et al., *Nature* 360:273 (1992); Sommer et al., *EMBO J.* 9:605 (1990); Trobner et al., *EMBO J.* 11:4693 (1992); Yanofsky et al., *Nature* 346:35 (1990); Greco et al., *Mol. Gen. Genet.* 253:615 (1997).

Chung et al., *Plant Molec. Biol.* 26:657 (1994), cloned a gene from rice, designated as the OsMADS1 gene, that encodes a MADS-domain containing protein. Chung et al. showed that transgenic tobacco that express the OsMADS1 gene were characterized by early flowering and reduced apical dominance. Accordingly, early flowering transgenic Impatiens can be produced that express a foreign protein having the MADS box sequence. Suitable early flowering genes include the PLENA gene, the SQUAMOSA gene, the DEFICIENS A gene, the GLOBOSA gene, the APTELA1 gene, the APETALA3 gene, the AGAMOUS gene, the OsMADS24 gene, the OsMADS45 gene, and the OsMADS1 gene.

The present invention, thus generally described, will be understood more readily by reference to the following examples, which are provided by way of illustration and are not intended to be limiting of the present invention. All publications, patents, and parent applications are herein incorporated by reference to the same extent as if each individual publication, patent, or parent application were specifically and individualy indicated to be incorporated by reference in its entirety.

EXAMPLES

Example 1

Shoot Regeneration of Impatiens

Impatiens Varieties Regenerated:
  Seed Impatiens:
    Super Elfin Scarlet, Super Elfin Twilight
  New Guinea Impatiens:
    Celebration Red, Celebration Deep Pink,
    Celebration Candy Pink, and Celebration Cherry Star
Explant Used:
  Shoot tips, hypocotyl tips and node regions.
Media:
  Medium according to Murashige and Skoog, *Physiol. Plant* 15: 473 (1962) (MS Medium) plus the following hormonal combinations:

TABLE 2

Zeatin 1 mg/L
2 ip 15 mg/L
BAP 15 mg/L
2 ip 20 mg/L, BAP 20 mg/L
2 ip 20 mg/L, Kinetin 20 mg/L
2 ip 20 mg/L, BAP 10 mg/L, IAA 0.01 mg/L
2 ip 20 mg/L, Kinetin 10 mg/L, IAA 0.01 mg/L
2 ip 20 mg/L, Zeatin 1 mg/L, IAA 0.01 mg/L
NAA 0.9 mg/L, BAP 2.25 mg/L
2, 4-D 0.8 mg/L, 2 ip 0.4 mg/L
NAA 0.2 mg/L, Zeatin 6 mg/L
NAA 0.05 mg/L, Zeatin 6 mg/L
TDZ 1 mg/L Results:

Axillary shoots can be induced from all of the above media. Thus, shoot regeneration from meristematic regions was not limited by any hormonal combinations. However, the preferred medium for the transformation research was MS salts plus NAA 0.05 mg/L and Zeatin 6 mg/L.

Example 2

*Agrobacterium tumefaciens* Preparation

Strain: GV 101.
Plasmid: pBI121, containing 35S promoter and GUS gene, and helper plasmid pGV101, containing the Ti plasmid Vir region.
Medium: YEB medium

TABLE 3

| | |
|---|---|
| Bacto beef extract | 5 g/L |
| Bacto beef extract | 1 g/L |
| Peptone | 5 g/L |
| Sucrose | 5 g/L |
| MgSO4 | $2 \times 10^{-3}$ M |
| pH 7.2 | |

Example 3

Selection of Transformed Impatiens Super Elfin Twilight

1. Shoot tips from in vitro grown Impatiens Super Elfin Twilight were harvested (about 1–1.5 cm length) and pre-cultured on a liquid MS medium containing TDZ 1 mg/L for 5 days. Then the shoot tips were subcultured on a solid MS medium supplemented with NAA 0.05 mg/L and Zeatin 6 mg/L for 48 hours.

2. A start culture of pBI121 and helper plasmid pGV101 was grown in *A. tumefaciens* strain GV101 for two days at 30° C. The plasmids pBI121 and pGV101 are described in FIG. 1.

3. A620 on cells was read and titer determined (1.0 A620=$5 \times 10^8$ cells/ml).

4. Cells were pelleted (4000 rpm, 10 minutes, 4° C.).

5. Cells were re-suspend in YEB to about $5 \times 10^8$ cells/ml.

6. The bacterial suspension was placed in a sterile petri dish.

7. Shoot tips were dipped in the bacterial suspension for several minutes, at which point the shoot tips were wounded with a needle.

8. The shoot tips were then blot dry treated on filter paper on a sterile plate.

9. The shoot tips were then transferred to fresh MS 0.05 mg/L NAA and 6 mg/L Zeatin medium without antibiotics for two days.

10. The shoot tips were next transferred to MS 0.05 mg/L NAA and 6 mg/L Zeatin medium with 500 mg/L carbenicillin, 100 mg/L. kanamycin, and 100 mg/L cefotaxmine.

11. The explants were then subcultured every week on the above selection medium until axillary shoots developed. Leaves from two different presumptive transformants designated 76-9 and 76-11 were analyzed for the presence of the reporter gene (GUS). GUS assays were performed according to known methods (See Jefferson et al., *EMBO J.* 6(13):3901–3907 (1987)).

(i) 50 mg X-gluc was dissolved in 1 ml DMSO and added to 100 ml of:
   10 mM EDTA disodium salt
   100 mM $NaPO_4$, pH 7.2
   0.5 mM $K_4Fe(CH)_6$
   0.1% Triton X-100
   pH to 7.3 with NaOH
Ref: McCabe, et al., *Biotechnology* 6:923 (1988).

(ii) 100 mg X-gluc was dissolved in 100 ml of 50 mM phosphate buffer.

Leaves from both 76-9 and 76-11 express GUS activity while non-transformed control leaf tissue was negative. Accordingly, transgenic Impatiens plants were obtained.

12. Transformants 76-9 and 76-11 developed into plants with roots, stems and leaves on the selection medium. Transformants 76-9 and 76-11 were transferred to soilless medium and placed on a mist bench in the greenhouse for approximately 3 weeks. The plants were then transferred to soilless medium in 4 inch pots and placed in the greenhouse to flower. Upon flowering, the 76-9 and 76-11 plants were crossed as the female parents to *I. wallerana* selections 7565R0-1-H-1 and 7565R-2-4-3-1. Seeds were collected from each of these four crosses, germinated in soilless medium and plants were recovered.

Example 4

According to the above examples New Guinea Impatiens Celebration Deep Pink was transformed and two transgenic plants were selected and assayed for GUS activity. These plants were designated, respectively, Line 1A and Line 1B. Both plants showed GUS activity when compared to non-transformed control.

What is claimed is:

1. A method for producing transgenic Impatiens plants, comprising the steps of:
   (a) introducing an expression vector into a plant tissue explant via Agrobacterium to produce a transformed explant, wherein said expression vector comprises a selectable marker gene and a second foreign gene, or
   (a') introducing two expression vectors into said plant tissue explant via Agrobacterium to produce a transformed explant, wherein one of said expression vectors comprises a selectable marker gene, and wherein the second of said expression vectors comprises a second foreign gene;
   (b) culturing said transformed explant on a selection medium;
   (c) culturing said transformed explant on regeneration medium; and
   (d) recovering fertile transgenic plants from said transgenic explants capable of transmitting said foreign gene to progeny.

2. The method of claim 1, wherein prior to introducing said explant, said explant is pre-cultured in (1) in MS medium comprising from approximately 0.5 mg/L to 2 mg/L TDZ followed by (2) MS medium comprising auxin and cytokinin.

3. The method of claim 2, wherein said auxin is approximately 0.05 to 0.2 mg/L NAA and said cytokinin is approximately 1 mg to 6 mg/L Zeatin.

4. The method of claim 2, wherein said first pre-culturing occurs for approximately 5 days and said second pre-culturing occurs for approximately 48 hours.

5. The method of claim 1, wherein said regeneration medium is MS medium with approximately 0.05 to 0.2 mg/L NAA and approximately 1 to 6 mg/L Zeatin.

6. The method of claim 1, wherein said marker is the nptII gene.

7. The method of claim 6, wherein said selection medium is MS medium comprising auxin, and cytokinin with 500 mg/L carbenicillin, 100 mg/L. kanamycin, and 100 mg/L cefotaxmine.

8. The method of claim 7, wherein said auxin is approximately 0.05 to 0.2 mg/L NAA and said cytokinin is approximately 1 to 6 mg/L Zeatin.

9. The method according to claim 7, wherein said regeneration medium is the same as said selection medium.

10. The method of claim 1, wherein said Impatiens plant tissue explant is selected from the group consisting of shoot tips, hypocotyl tips, and node regions.

11. The method of claim 10, wherein said Impatiens plant tissue explant is obtained from Impatiens shoot tip.

12. The method of claim 1, wherein said expression vector that comprises said second foreign gene further comprises a promoter, wherein said promoter is selected from the group consisting of Cauliflower Mosaic Virus (CaMV) 35S promoter, the enhanced 35S promoter, the UBQ3 promoter, the UBQ10 promoter, the UBQ11 promoter, the UBQ14 promoter, the TEFA 1 promoter, the rolC promoter, and the Commelina Yellow Mottle Virus promoter, wherein the expression of said second foreign gene is under the control of said promoter.

13. The method of claim 11, wherein said promoter is a CaMV 35S promoter.

14. The method of claim 1, wherein the expression of said second foreign gene confers resistance to disease caused by an organism selected from the group consisting of virus, bacterium, fungus, and insect.

15. The method of claim 1, wherein said second foreign gene confers resistance to a virus, and wherein said virus resistance gene disrupts the function of said virus, and wherein said virus-disrupting gene is selected from the group consisting of viral coat protein, 2'-5' oligonucleotide synthetase, viral genome antisense RNA, and pokeweed antiviral protein.

16. The method of claim 1, wherein said second foreign gene confers resistance to an insect, and wherein said insect resistance gene is selected from the group consisting of tryptophan decarboxylase, lectin, and *Bacillus thuringiensis* toxin.

17. The method of claim 16, wherein said lectin is *Galanthus nivalis* lectin.

18. The method of claim 1, wherein said second foreign gene confers resistance to a bacterium or a fungus, and wherein said second foreign gene encodes a polypeptide selected from the group consisting of chitinase, a β-1,3-glucanase, ribosome-inactivating protein, lytic peptide, and plant defensin.

19. The method of claim 18, wherein said plant defensin is radish seed Rs-AFP2.

20. The method of claim 1, wherein said second foreign gene is operatively linked with a DNA molecule encoding pea vicilin signal peptide.

21. The method of claim 1, wherein said transgenic Impatiens comprises an expression vector that further comprises a third foreign gene.

22. The method of claim 1, wherein said second foreign gene encodes chitinase, and wherein said third foreign gene encodes β-1,3-glucanase.

23. The method of claim 1, wherein the expression of said second foreign gene confers insensitivity to ethylene, and wherein said second foreign gene encodes a mutated ethylene receptor.

24. The method of claim 23, wherein said mutated ethylene receptor gene is the Arabidopsis etr-1 gene or a tomato NR gene.

25. The method of claim 1, wherein said second foreign gene is the Vitreoscilla hemoglobin gene.

26. The method of claim 1, wherein said second foreign gene is an isopentenyl transferase gene, wherein the expression of said isopentenyl transferase gene is under the control of a promoter of a senescence-associated gene.

27. The method of claim 26, wherein said promoter is the Arabidopsis SAG12 gene promoter.

28. The method of claim 1, wherein said second foreign gene encodes a polypeptide having a MADS box domain.

29. The method of claim 28, wherein said second foreign gene is selected from the group consisting of the PLENA gene, the SQUAMOSA gene, the DEFICIENS A gene, the GLOBOSA gene, the APTELA1 gene, the APETALA3 gene, the AGAMOUS gene, the OsMADS24 gene, the OsMADS45 gene, and the OsMADS1 gene.

30. The method of claim 1, wherein said second foreign gene encodes a protein that modifies plant habit.

31. The method of claim 1, wherein said second foreign gene confers resistance to INSV, wherein said second foreign gene encodes INSV S, M, and L RNAs.

32. The method of claim 1, wherein said second foreign gene confers resistance to TSWV, wherein said second foreign gene encodes TSWV viral movement protein.

33. The method of claim 1, wherein said second foreign gene confers fragrance, wherein said second foreign gene is selected from the group consisting of linalool synthase gene and limonene synthase gene.

34. The method of claim 1, wherein said second foreign gene confers resistance to drought, salinity or a cold, wherein said second foreign gene is selected from the group consisting of *E. coli* MnSOD gene, asparagine synthetase gene or promoter, Delta$^1$-Pyrroline-5-Carboxylate Synthetase gene, bacterial fructan gene, CAP85 and CAP160 genes, and trg-31.

35. A fertile transgenic Impatiens plant produced by the method of claim 1.

36. A fertile transgenic Impatiens plant having stably integrated in the plant genome a foreign gene, wherein said transgenic Impatiens plant is capable of transmitting said foreign gene to progeny.

37. Seeds and progeny of said transgenic Impatiens plant of claim 36 which are transformed with said foreign gene.

* * * * *

UNITED STATES PATENT AND TRADEMARK OFFICE
Certificate

Patent No. 6,121,511                                                  Patented: September 19, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Tau-San Chou, West Chicago, IL; and Joyce Van Eck, Ithaca, NY.

Signed and Sealed this Tenth Day of February 2004.

AMY NELSON
*Supervisory Patent Examiner*
Art Unit 1638